United States Patent
Strickland et al.

(10) Patent No.: US 8,781,550 B2
(45) Date of Patent: Jul. 15, 2014

(54) COMMUNICATION PROTOCOL THAT SUPPORTS STRUCTURED COLLECTION PROCEDURES USED IN DIABETES CARE

(75) Inventors: Raymond Strickland, Indianapolis, IN (US); Ulrich Porsch, Weinheim (DE); John Price, McCordsville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 798 days.

(21) Appl. No.: 12/976,102

(22) Filed: Dec. 22, 2010

(65) Prior Publication Data
US 2012/0095317 A1    Apr. 19, 2012

Related U.S. Application Data

(60) Provisional application No. 61/393,536, filed on Oct. 15, 2010.

(51) Int. Cl.
| | |
|---|---|
| *A61B 5/05* | (2006.01) |
| *A61B 5/145* | (2006.01) |
| *G06F 19/00* | (2011.01) |
| *A61B 5/021* | (2006.01) |
| *A61B 5/00* | (2006.01) |
| *A61B 5/0205* | (2006.01) |
| *A61B 5/1455* | (2006.01) |

(52) U.S. Cl.
CPC .............. *G06F 19/3406* (2013.01); *A61B 5/021* (2013.01); *A61B 5/4839* (2013.01); *A61B 5/14532* (2013.01); *A61B 5/0022* (2013.01); *A61B 5/02055* (2013.01); *A61B 5/14551* (2013.01)
USPC ........................... 600/345; 600/347; 600/365

(58) Field of Classification Search
USPC .......................... 600/309, 316, 345–347, 365
See application file for complete search history.

(56) References Cited

U.S. PATENT DOCUMENTS

| | | | |
|---|---|---|---|
| 2010/0161352 A1* | 6/2010 | Lim et al. ......................... | 705/3 |
| 2010/0198142 A1* | 8/2010 | Sloan et al. ..................... | 604/66 |

OTHER PUBLICATIONS

Part 10417: Device Specialization-Glucose Meter, IEEE Std 11073-10471, May 8, 2009.*
"ISO/IEEE Health Informatics Personal Health Device Communication Part 10417: Device Specialization Glucose Meter; ISO/IEEE 11073-10417:2010 (E)", IEEE Standard, IEEE; Piscataway, NJ (May 5, 2010).
Part 20601: Application Profile—Optimized Exchange Protocol, IEEE Std 11073-20601 Sep. 26, 2008.
Part 10417: Device Specialization-Glucose Meter, IEEE Std 11073-10417, May 8, 2009.
Continua Design Guidelines 2010, Oct. 1, 2010.

* cited by examiner

*Primary Examiner* — Michael D'Angelo
(74) *Attorney, Agent, or Firm* — Harness, Dickey

(57) ABSTRACT

A computer-implemented diabetes management system is provided for configuring a structured collection procedure implemented on a collection device having a meter that measures the concentration of glucose in blood. The system includes: a collection application that executes a structured collection procedure for obtaining measurement data from the meter and provides access to the measurement data via a communication protocol defined in accordance with IEEE standard 11073-20601; a configuration application that accesses and manipulates the parameters of the structured collection procedure using a set of action commands, where the set of action commands are defined in compliance with the communication protocol; and a collection interface that receives an action command from the configuration application, executes the received action command and issues a response command in response thereto, where the response command is defined in compliance with the communication protocol.

9 Claims, 7 Drawing Sheets

| Parameters | bG (Biosensor) Measurement | Meal Size (S, M, or L) | Energy Level (0-5) | Timing | Adherence Criteria | Guidance | Options |
|---|---|---|---|---|---|---|---|
| bG Level Trending | | | | | | | |
| Entry Criteria | | | | MM-DD-YYYY | Affirms Guidance, If Not Add 1 Day to Timing | Are You Willing to Conduct A Test Over 3 Consecutive Days? | |
| Exit Criteria | | | | MM-DD-YYYY | Entry Timing + 3 Days | | |
| Before Breakfast | Y | | Y | HHMM | | Please Indicate Energy Level | 1 |
| n₁ Hours After Breakfast | Y | Y | Y | n₁ | ± 30 Minutes of n₁ | Please Indicate Meal Size & Energy Level | |
| Before Lunch | Y | | Y | | | Please Indicate Energy Level | |
| n₂ Hours After Lunch | Y | Y | Y | n₂ | ± 30 Minutes of n₁ | Please Indicate Meal Size & Energy Level | |
| Before Dinner | Y | | Y | | | Please Indicate Energy Level | |
| n₃ Hours After Dinner | Y | Y | Y | n₃ | ± 30 Minutes of n₁ | Please Indicate Meal Size & Energy Level | |
| Before Bed | Y | | Y | | | Please Indicate Energy Level | |

Fig-5

COMMUNICATION PROTOCOL THAT SUPPORTS STRUCTURED COLLECTION PROCEDURES USED IN DIABETES CARE

CROSS-REFERENCE TO RELATED APPLICATIONS

This application claims the benefit of U.S. Provisional Application No. 61/393,536, filed on Oct. 15, 2010. The entire disclosure of the above application is incorporated herein by reference.

FIELD

The present disclosure relates to communication protocol for medical devices used for diabetes care and, more particularly, to a communication protocol that supports a structured collection procedure implemented by the medical devices.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose concentration, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Clinicians generally treat diabetic patients according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes. However, such guidelines do not specify biomarker collection procedures for parameter adjustments to support specific therapies used in optimizing a diabetic patient's therapy. Subsequently, diabetic patients often must measure their glucose levels with little structure for collection and with little regard to lifestyle factors. Such unstructured collection of glucose levels can result in some biomarker measurements lacking interpretative context, thereby reducing the value of such measurements to clinicians and other health care providers. Thus, there is a need to provide structured collection procedures for diagnostic or therapy support of a patient with diabetes or other chronic diseases.

Patients with diabetes and their healthcare professionals interact with a variety of medical devices and systems to help manage the disease, including performing structured collection procedures. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol. IEEE 11073 is an exemplary communication standard that addresses interoperability and communication amongst medical devices such as blood pressure monitors, blood glucose monitors and the like. Within the context of such communication protocol, there is a further need to support the structured collection procedures implemented by the medical devices.

The background description provided herein is for the purpose of generally presenting the context of the disclosure.

SUMMARY

A computer-implemented diabetes management system is provided for configuring a structured collection procedure implemented on a collection device having a meter that measures the concentration of glucose in blood. The system includes: a collection application that executes a structured collection procedure for obtaining measurement data from the meter and provides access to the measurement data via a communication protocol defined in accordance with IEEE standard 11073-20601; a configuration application that accesses and manipulates the parameters of the structured collection procedure using a set of action commands, where the set of action commands are defined in compliance with the communication protocol; and a collection interface that receives an action command from the configuration application, executes the received action command and issues a response command in response thereto, where the response command is defined in compliance with the communication protocol.

In one aspect of this disclosure, the parameters of the structured collection procedure are further defined as reminders for one or more collection events associated with the structured collection procedure such that the configuration application uses the set of action commands to at least one of read a reminder for a collection event or set a reminder for a collection event.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

FIG. 5 is a chart that conceptually illustrates an exemplary structured collection procedure;

Figure 1:
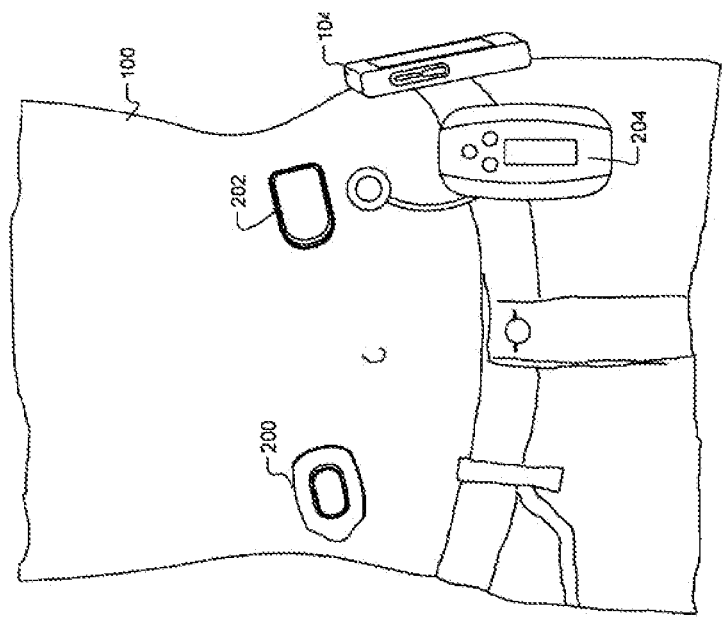
FIG. 1 is a diagram showing a patient and a treating clinician.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Referring to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
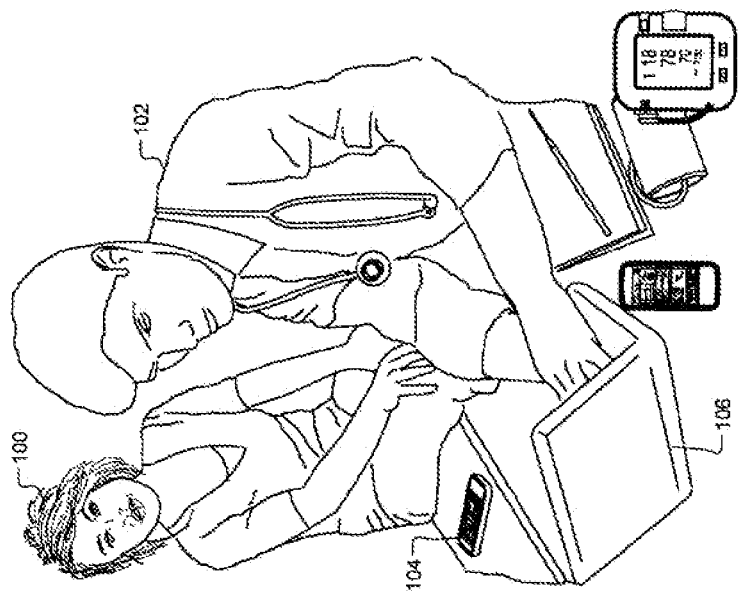
FIG. 2 is a diagram showing the patient with a continuous glucose monitor (CGM), an ambulatory durable insulin infusion pump, an ambulatory non-durable insulin infusion pump, and a diabetes manger.

Referring to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in a scheduled manner in the form of a basal dose, which maintains a predetermined insulin level in the blood of the patient 100. Additionally, insulin can be delivered in the form of a bolus dose, which raises the amount of insulin in the blood of the patient 100 by a predetermined amount.

Figure 3:
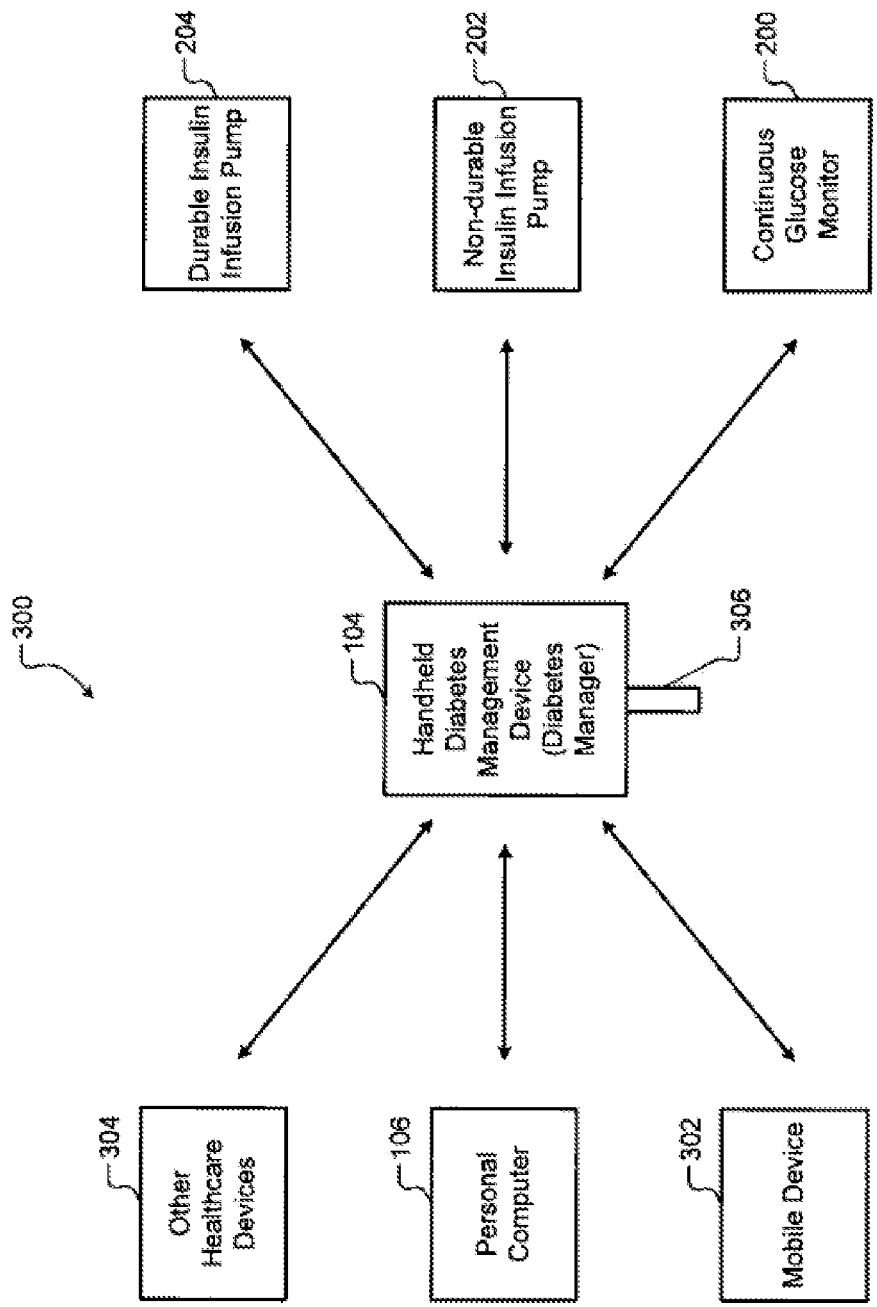
FIG. 3 is a block diagram showing an exemplary diabetes management system used by patients and clinicians to manage diabetes.

Referring to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the insulin pump 204 or the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary Gazell wireless protocol developed by Nordic Semiconductor, Inc.

Additionally, the diabetes manager 104 includes a blood glucose meter (BGM) and a port that communicates with the BGM (not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100. To facilitate collection of blood glucose measures, the diabetes manager 104 may executes one or more structured collection procedures as further described below.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 4:
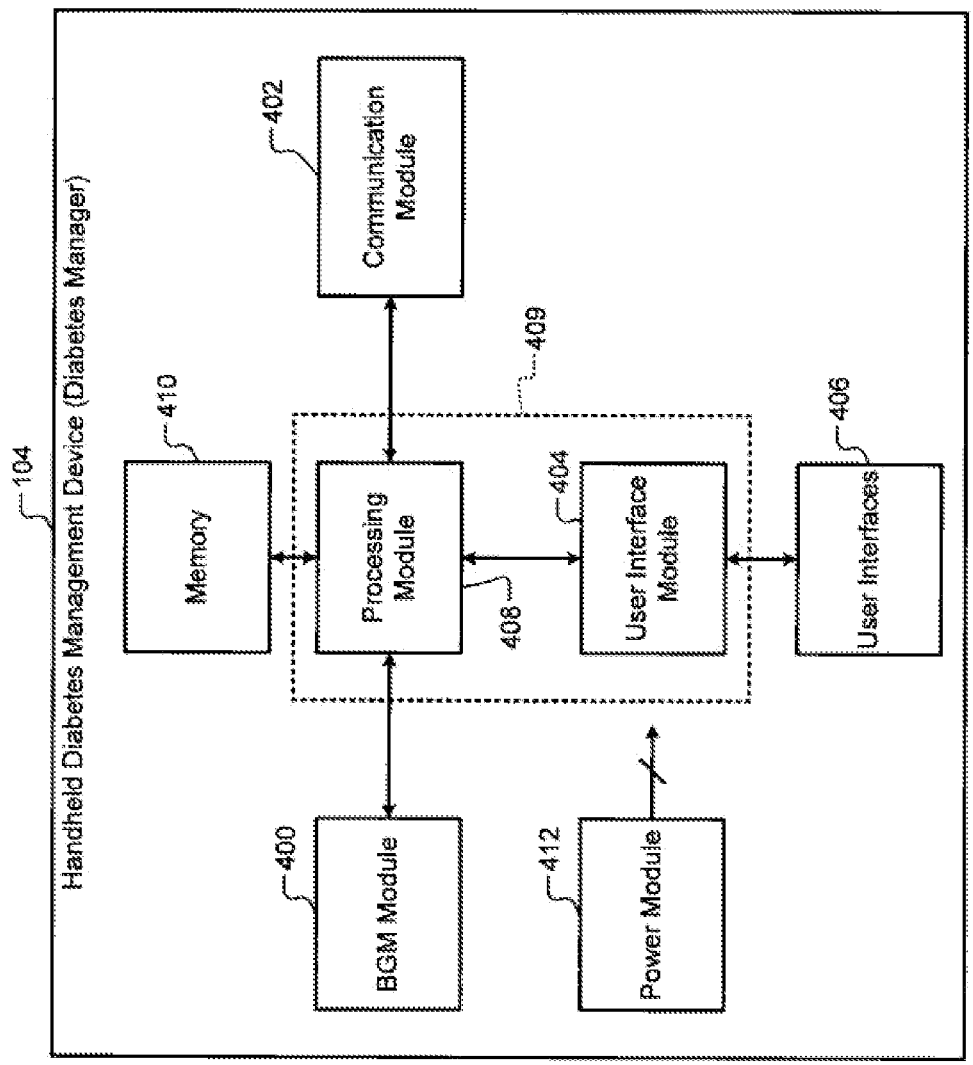
FIG. 4 is a functional block diagram of a diabetes manager.

An exemplary diabetes manager 104 is further described in relation to FIG. 4. The diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

For purposes of this disclosure, the diabetes manager 104 serves as a collection device. However, the collection device can be any portable electronic device that can provide an acquisition mechanism for determining and storing physiological measures of a person. For example, self-monitoring blood glucose meters and continuous glucose monitor devices are examples of collection devices used in diabetes care. While this disclosure makes reference to diabetes care, it is readily understood that the concepts disclosed herein can be applied to other types of chronic diseases and/or collection devices.

In the diabetes care domain, a structured test or structure collection procedure is a particular type of treatment plan. FIG. 5 conceptually illustrates an exemplary structured collection procedure 500 comprised of a plurality of parameters that define the procedure. A structured collection procedure is primarily comprised of a series of planned actions or collection events 510 for obtaining measurement data using the collection device. Each collection event is a request for a physiological measure obtained using the collection device or other input by the patient into the collection device. In the illustrated procedure, the requests are for a bG measurement. A given collection event may require additional input such as an indication of meal size or an indication of the patient's energy level.

In addition to a series of collection events, the structured collection procedure 500 may include other types of parameters such as a medical use case 512, an entry criterion 514, an adherence criterion 516 and an exit criterion 518. Medical use case 512 provides an indication of when the particular procedure may be applicable. In this case, the collection procedure is helpful for determining trends in blood glucose (bG) levels of a patient and/or relationships between blood glucose and other parameters, such as time of day, meal size, energy level, etc. Entry criterion 514 establishes the conditions needed to be met prior to obtaining a physiological measure from the patient. Adherence criterion 516 is used to assess qualitatively whether a given collection event was performed. Exit criterion 518 establishes the conditions needed to be met prior to exiting the structured collection procedure. It is readily understood that other types of parameters may be used to define a structured collection procedure. Further information regarding structure collection procedures may be found in U.S. patent application Ser. No. 12/643,338 (WinPat 25378) entitled "Structured Testing Method for Diagnostic or Therapy Support of a Patient with a Chronic Disease and Devices Thereof" which is incorporated by reference herein.

Figure 7:
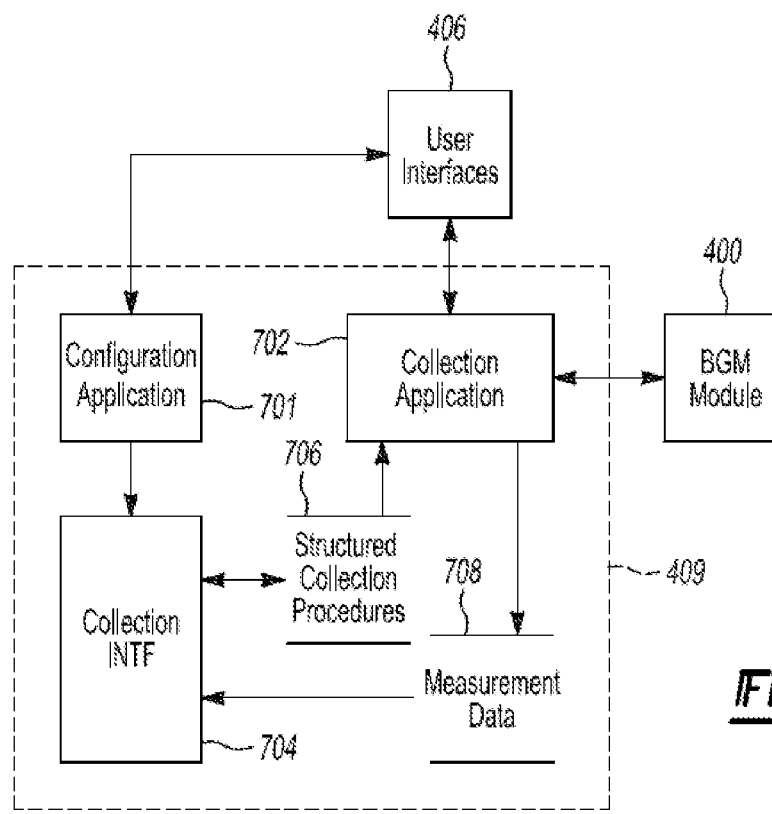
FIG. 7 is a diagram depicting an exemplary system that supports remote configuration of such structure collection procedures.

Structured collection procedures are typically implemented on a collection device, such as diabetes manager 104. FIG. 7 depicts an exemplary system 700 that supports remote configuration of such structure collection procedures by a configuration application 701. In an exemplary embodiment, the application processing module 409 of the diabetes manager 104 is further defined to support configuration. The application processing module 409 includes a configuration application 701, a collection application 702 and a collection interface 704; each of these components may be implemented as computer executable instructions in a data store of the collection device. One or more structured collection procedures may also reside in a data store 706 accessible to the collection application 702.

During operation, the collection application 702 executes a structured collection procedure to obtain measurement data from the patient. In a simplified example, the collection application 702 may interact with a user interface 406 to prompt a patient to take a glucose measure. The patient may be prompted at a particular time of day as specified by the structured collection procedure. The collection application 702 is interfaced with the BGM module 400 to receive blood glucose measures obtained from the patient and store such measures in a data store residing on the collection device. The collection application 702 may also interact with the user interface 406 to obtain other input from the patient in accordance with the structured collection procedure.

The collection interface 704 in turn provides access to the blood glucose measures and other related measurement data. In the exemplary embodiment, measurement data is accessed via the collection interface 704 using a communication protocol defined in accordance with IEEE standard 11073-20601. In the case of blood glucose measures, the collection interface 704 may implement a device specialized communication protocol as defined by IEEE standard 11073-10417. For other types of measures, it is understood that the collection interface 704 may implement the applicable specialized communication protocol.

Over time, the parameters associated with a structured collection procedure residing on the collection device may need to be configured or otherwise modified by a tending healthcare provider. The configuration application 701 provides the mechanism by which the parameters of a structured collection procedure may be accessed and manipulated by the healthcare provider. For example, the configuration application 701, interacting with suitable user interfaces, enables the healthcare provider to select a structured collection procedure associated with a given patient. Parameters associated with the select collection procedure are then displayed to the healthcare provider. The healthcare provider may modify and save one or more of the parameters associated with the selected collection procedure. In one exemplary embodiment, the configuration application 701 may reside on the collection device. In this embodiment, the configuration application 701 interacts with the user interfaces 406 residing on the collection device as shown in FIG. 7.

Figure 8:
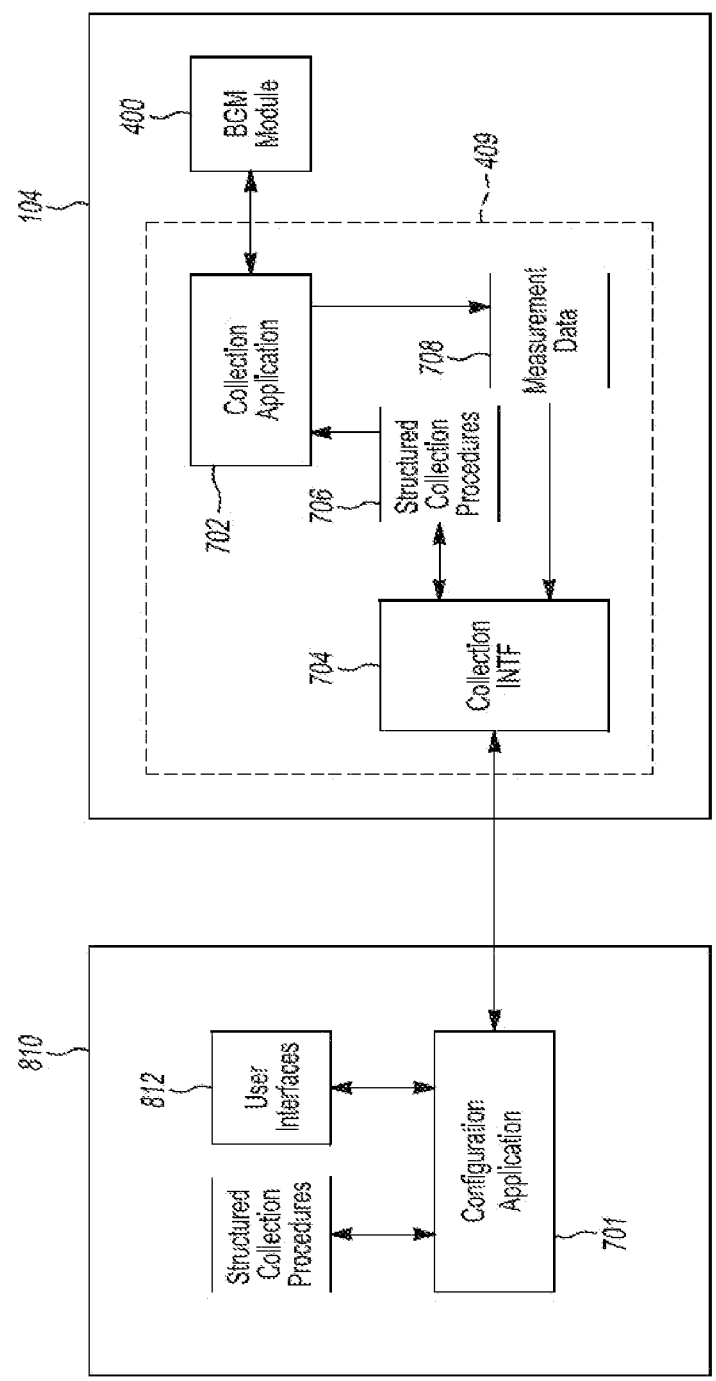
FIG. 8 is a diagram depicting another exemplary system that supports remote configuration of such structure collection procedures.

In another exemplary embodiment, the configuration application 701 may reside on a device 810 distinct and remote from the collection device as shown in FIG. 8. For example, the device 810 may be a personal computer that resides with the healthcare provider. In this embodiment, the configuration application 701 interacts with user interfaces 812 residing on the device 810 to access and manipulate the structured collection procedure, where the structured collection procedures are stored in a data store on the device 810. Once healthcare provider has updated a given structure collection procedure locally, the configuration application 701 will then interact with the collection interface to update the corresponding structured collection procedure on the collection device.

To do so, the configuration application 701 interfaces with the collection interface 704 using a set of action commands to update parameters of a structured collection procedure residing at the collection device. Of note, the set of action commands are defined in compliance with the communication protocol used to access the measurement data. In the exemplary embodiment, the collection interface 704 accesses the blood glucose measures using the IEEE standard 11073-10417. Thus, the set of action commands used to access and manipulate the parameters of a structured collection procedure are defined as a private extension of the IEEE standard 11073-10417 as will be further described below.

ISO/IEEE 11073 standard enables communication amongst medical devices and other computer systems. By way of background, ISO/IEEE 11073 standard is based on an object oriented systems management paradigm. The overall system model is divided into three principal components: the domain information model (DIM), the service model, and the communication model. These three components work together to represent data, define data access and command methodologies and communicate the data from an agent to a manager. ISO/IEEE 11073-20601 may be referenced for a detailed description of the modeling constructs although each is described briefly below.

Figure 9:
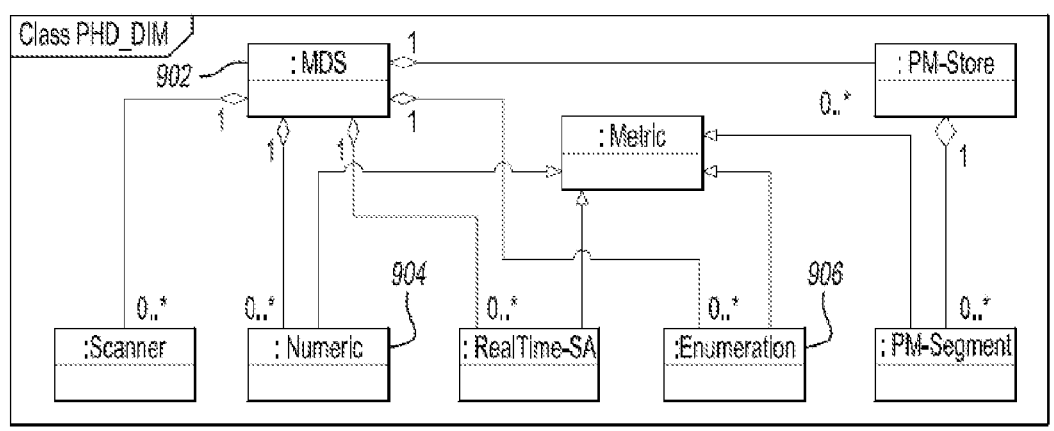
FIG. 9 is a class diagram for a personal health device defined in accordance with ISO/IEEE 11073-20601.

The domain information model is a hierarchical model that describes an agent as a set of objects. These objects and their attributes represent the elements that control behavior and report on the status of the agent and the data that an agent can communicate to a manager. With reference to FIG. 9, a class diagram for a personal health device is defined in accordance with ISO/IEEE 11073-20601. The Medical Device System class 902 is the root class of the device and contains attributes defining the device itself. Exemplary attributes include the type of device, i.e., glucose meter or insulin pump, manufacturer and model information and registered certification information. All other object classes are derived from the MDS class. For example, the Numeric class represents numeric measurements such as bG, carbohydrates, bolus amount, etc; whereas, the enumeration class represents status information and/or annotation information. For brevity purposes, a description is not provided for all of the classes shown in the figure.

Communication between the agent and the manager is defined by the application protocol in ISO/IEEE 11073-20601. The service model defines the conceptual mechanisms for the data exchange services. Object access services, such as Get, Set, Action and Event Reports, are mapped to messages that are exchanged between the agent and the manager. Protocol messages within the ISO/IEEE 11072 series of standards are defined in ASN.1. The messages defined in ISO/IEEE 11073-20601 can coexist with messages defined in other standard application profiles defined in the ISO/IEEE 11072 series of standards.

In general, the communication model supports the topology of one or more agents communicating over logical point-to-point connections to a single manager. More specifically, the communication model defines the construct of an application protocol data unit (APDU). ADPUs are data packets exchanged between agents and managers. For each logical point-to-point connection, the dynamic system behavior is defined by a connection state machine as specified in ISO/IEEE 11073-20601.

Two styles of configuration are defined in ISO/IEEE 11073-20601: standard and extended. Standard configurations are defined in the ISO/IEEE 11073-104zz specializations (such as the ISO/IEEE 11073-10417 Glucose Device specialization) and are assigned a well-known identifier (Dev-Configuration-Id). The usage of a standard configuration is negotiated at association time between the agent and the manager. If the manager acknowledges that it understands and wants to operate using the configuration, then the agent can begin sending measurements immediately. If the manager does not understand the configuration, the agent provides the configuration prior to transmitting measurement information.

In extended configurations, the agent's configuration is not predefined in a standard. The agent determines which objects, attributes, and values will be used in a configuration and assigns a configuration identifier. When the agent associates with a manager, it negotiates an acceptable configuration. Typically, the manager does not recognize the agent's configuration on the first connection, so the manager responds that the agent needs to send the configuration information as a configuration event report. If, however, the manager already understands the configuration, either because it was preloaded in some way or the agent had previously associated with the manager, then the manager responds that the configuration is known and no further configuration information needs to be sent.

Figure 6:
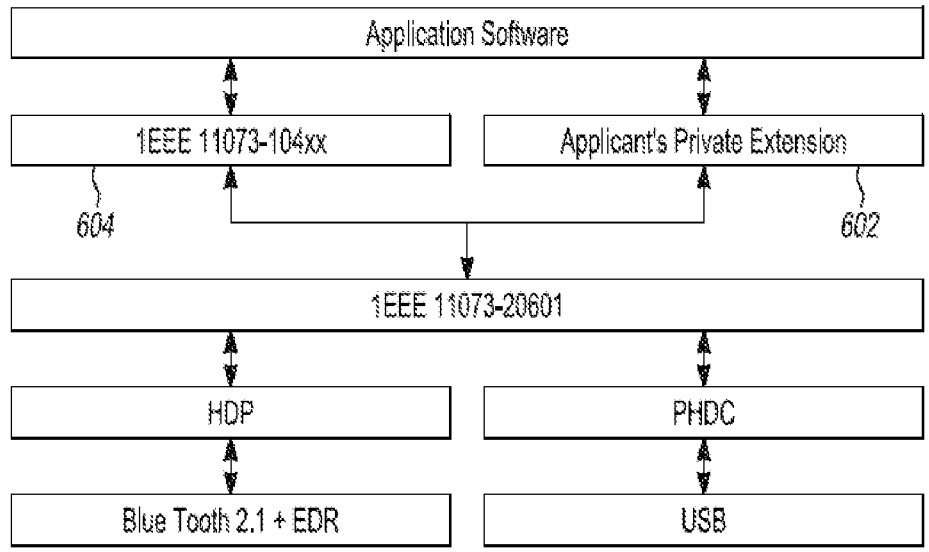
FIG. 6 is a block diagram depicting how applicant's private extension relates to the standardized communication protocols.

With reference to FIG. 6, this disclosure defines an extension 602 to these configurations, i.e., applicant's private extension, which is not published in any of the ISO/IEEE 11073-104xx device specializations 604. Applicant's private extension 602 relationship to the standardized communication protocols is shown in FIG. 6. Generally speaking, implementation of this private extension 602 defines the attributes and services to support the transfer and execution of specific commands and data. A basic framework for the private extension is first described below. Within this framework, a set of action commands that support structured collection procedures are then presented by this disclosure. The set of action commands are used by the configuration application 701 and the collection interface 704 to access and manipulate the parameters of structured collection procedures. It is readily understood that other types of commands sets can also fall within the framework for the private extension.

In an exemplary embodiment of applicant's private extension, each agent device has one MDS object. This top-level MDS object is instantiated from the MDS class. The MDS object represents the identification and status of the agent through its attributes. Beyond the class definition provided by the IEEE standards, additional standardized classes may be supported by the agents and managers in accordance with applicant's private extension. The additional standardized classes are referred to herein as RPC classes. RPC private nomenclature codes are assigned from the manufacturer-specific range of private term codes (0xF000-0xFBFF) within the object oriented partition category (MDC_PART-OBJ). The partition number for object oriented classes and objects is 1.

The attributes for each RPC class are defined in tables that specify the name of the attribute, its value and its qualifier. The qualifiers mean M—attribute is mandatory, C—attribute is conditional and depends on the condition stated in the remark or value column, R—attribute is recommended, NR—attribute is not recommended, and O—attribute is optional. Mandatory attributes shall be implemented by an agent. Conditional attributes shall be implemented if the condition applies and may be implemented otherwise. Recommended attributes should be implemented by the agent. Not recommend attributes should not be implemented by the agent. Optional attributes may be implemented on an agent.

RPC classes that instantiate numeric type objects are created as they exist in the device. These numeric type objects represent additional result data that can be obtained from the device in the same manner they are obtained from the device specialization. These objects shall be added to the device attribute value map for authenticated managers. Attributes common across all of the RPC numeric objects are set forth in Appendix A. Furthermore, applicant's private extension has defined a few RPC numeric objects available to system designers Likewise, definitions for these common RPC numeric objects are set forth in Appendix A. Applicant's private extension also defines a few RPC enumeration objects as set forth in Appendix B.

Applicant's private extension further defines an application protocol data unit as set forth below. An APDU represents the top-level message frame of the personal health device protocol. The extended APDU is added as an extension to the standard list of APDUs defined in the ISO/IEEE 11073-20601 specification.

```
Apdu Type ::=CHOICE {
  aarq [57856] AarqApdu, -- Association Request [0xE200]
  aare [58112] AareApdu, -- Association Response [0xE300]
  rlrq [58368] RlrqApdu, -- Association Release Request [0xE400]
  rlre [58624] RlreApdu, -- Association Release Response [0xE500]
  abrt [58880] AbrtApdu, -- Association Abort [0xE600]
  prst [59136] PrstApdu, -- Presentation APDU [0xE700]
  prrp [61440] PrrpApdu - applicant's extended APDU [0xF000]}
```

A presentation APDU as defined in ISO/IEEE 11073-20601 is simply an octet string. Applicant's extended APDU adds a 16-bit CRC in order to ensure data integrity beyond the level provided by the transport and the ISO/IEEE 11073-20601 concept of reliable data channels. With this CRC, corrupted data can be detected by the application. This CRC covers the entire "RPC" part of the command invoke and command response APDUs.

```
PrrpApdup ::= SEQUENCE {
  data   OCTET STRING, (ENCODED VERSION OF DataApdu)
  crc    INT-U16 (checksum over the entire data field)
}
```

Applicant's extended APDU shall encapsulate unconfirmed Action Argument and confirmed Event Report Data APDUs defined by the ISO/IEEE 11073-20601 standard as follows:

```
ActionArgumentSimple ::= SEQUENCE {
    obj-handle      HANDLE
    action-type     OID-Type,    --From the nom-part-obj partition
                                 --Subpartition ACT (MDC_ACT_*)
    Action-info-args ANY DEFINED BY action-type
}
EventReportArgumentSimple ::=SEQUENCE {
    obj-handle      HANDLE
    event-time      Relative Time,
    event-type      OID-Type     --From the nom-part-obj partition
                                 --Subpartition NOTI (MDC_NOTI_*)
    event-info      ANY DEFINED BY event-type
}
```

The approach used to invoke applicant's defined commands is to extend the MDS object methods with applicant defined actions. The ISO/IEEE 11073-20601 unconfirmed action service uses the ActionArgumentSimple structure previously discussed in this disclosure.

For the purposes of this specification, the fields would have the following values:

| | |
|---|---|
| handle | 0 (for the MDS object) |
| action-type | manufacturer specific code for applicant defined actions |
| action-info-args | manufacturer specific structure for each applicant defined action |

In order to invoke an applicant defined command, a manager would populate the action-type and action-info-arts of the ActionArgumentSimple object as follows:

| | |
|---|---|
| action-type | MDC_ACT_RPC_COMMAND_INVOKE |
| action-info-args | RpcCommandArguments |

The data objects used for command invocation action-info-args are defined as follows:

```
RpcCommandArguments ::= SEQUENCE {
    cmd-subcmd  INT-U16;   //Command/subcommand combined
    arguments   RpcDataArguments [ ];
}
RpcDataArguments ::= SEQUENCE {
    type    INT-U16;
    data    ANY DEFINED BY type
}
```

The encoding of ANY DEFINED BY is defined in ISO/IEEE 11073-20601 as follows: The ANY DEFINED BY type (ASN.1 1988/90) or the instance-of type (ASN.1 1994) is encoded by a header of a length field to specify the number of octets in the encoding of the selected value that follows. The length element shall be expressed as the number of bytes (octets) contained in the value element. An empty argument shall be indicated with the type element set to RPC_ARG_TYPE_EMPTY, the length element set to 2 and the value element set to zero as an INT-U16. An RpcCommandArguments structure which contains a cmd-subcmd value that requires no arguments will include a single RpcDataArguments element indicating an empty argument.

The approach used to return data as a result of an applicant defined command invocation is to extend the MDS event reports with applicant defined events. The ISO/IEEE 11073-20601 confirmed notification service uses the EventReportArgumentSimple structure previously discussed in this disclosure. For the purposes of the specification, the fields would have the following values:

| | |
|---|---|
| Handle | 0 (for the MDS object) |
| event-time | 0 (event time is not used for applicant actions) |
| event-type | manufacturer specific code for applicant defined command responses. - |
| event-info | manufacturer specific structure for each applicant defined response. |

In order to respond to an applicant defined command, an agent would populate the event-type and event-info of the EventReportArgumentSimple object as follows:

| | |
|---|---|
| Event-type | MDC_NOTI_RPC_COMMAND_RESPONSE |
| event-info | RpcDataArguments [ ] |

The RpcDataArguments object is the same as is defined for applicant defined actions.

Methods (actions) available for the MDS object are defined in the table below. These methods are invoked using the ACTION service. In the table, the Method/Action column defines the name of the method. The Mode column defines whether the method is invoked as an unconfirmed action (i.e., roiv-cmip-action) or a confirmed action (i.e., roiv-cmip-confirmed-action). The Action-type column defines the nomenclature ID to use in the action-type field of an action request and response. The action-info-args column defines the associated data structure to use in the action message for the action-info-args field of the request. The Resulting action-info-args column define the structure to use in the action-info-args of the response.

| Method/Action | Mode | Action-type | Action-info-args | Resulting action-info-args |
|---|---|---|---|---|
| RFC-Command-Invoke | Unconfirmed | MDC_ACT_RPC_COMMAND_INVOKE | RpcCommandArguments | n/a |

This method allows the manager to invoke an applicant defined system command.

Potential events sent by the RPC object are defined in the table below. A manager shall support all methods defined in the table.

| Method/Action | Mode | Event-type | Event-info Parameter | Event-reply-info |
|---|---|---|---|---|
| RPC-Data-Event | Confirmed | MDC_NOTI_RPC_COMMAND_RESPONSE | RpcDataArguments | RpcDataArguments |
| RPC-Error-Event | Confirmed | MDC_NOTI_RPC_ERROR_RESPONSE | RpcDataArguments | RpcDataArguments |

For the command response event, after the execution of an applicant defined command has been requested via the ACTION service, the agent will process the command, sub-command and parameter objects. If there are no command parameter errors, the result will be an agent-initiated event report reflecting the result of successful command processing. In the case of command success, the event report will contain a command-specific result string of data as defined by this specification.

For the error response event, after the execution of an applicant defined command has been requested via the ACTION service, the agent will process the command, sub-command and parameter objects. If there are parameter errors, the result will be an agent-initiated event report specifying the parameter error. If a manager receives an RPC_ERR_HARDWARE or RPC_ERR_APPLICATION response, the manager should invoke the RPC Read and Clear Status command to retrieve further error information available from the device.

Within this framework, a set of action commands that support structured collection procedures is further described below. For example, a structured collection procedure is readable by using a Read ST Configuration command in conjunction with the subcommands listed in this section. The command for reading ST configuration is RPC_CMD_READ_ST_CONFIGURATION and has a value of 0x8000. It must be "OR-ed" with one of the read ST configuration subcommand values to form a complete command-subcommand value. Six exemplary subcommands are set forth below.

First, the Read 3-Day Reminders is a command that return an array of ST Reminder structures, the number of ST Reminder structures returned is device dependent. The ID values for the returned structures shall be one of Before Breakfast, Before Lunch, Before Dinner or Before Bedtime. An exemplary command definition is as follows.
Command/Subcommand=0x8001
Input Parameters:
　None
Output Parameters:

| Reminder Array[ ] | RpcStReminder (section 6.1.2.8) |
|---|---|

RPC Command Invocation:

| cmd-subcmd | RPC_CMD_READ_ST_CONFIGURATION \| RPC_SUBCMD_READ_3D_REMINDERS |
|---|---|
| RpcDataArguments[0].type | RPC_ARG_TYPE_EMPTY |
| RpcDataArguments[0].length | 0x0002 |
| RpcDataArguments[0].value | 0x0000 |

RPC Command Response:

| obj-handle | 0x0000 |
|---|---|
| event-time | 0xFFFFFFFF |
| event-type | MDC_NOTI_RPC_COMMAND_RESPONSE |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[n].value | RpcStReminder structure |

Second, the Read 3-Day Status is a command shall return an unsigned integer value which indicates whether the activation status is enabled or disabled. An exemplary command definition is as follows.
Command/Subcommand=0x8002
Input Parameters:
　None
Output Parameters:

| Activation Status | OperationalState (See ISO/IEEE 11073-20601) |
|---|---|

RPC Command Invocation:

| | |
|---|---|
| cmd-subcmd | RPC_CMD_READ_ST_CONFIGURATION \| RPC_SUBCMD_READ_3D_STATUS |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_OPERATIONAL_STATE |
| RpcDataArguments[0].length | 0.0002 |
| RpcDataArguments[0].value | 0x0001 = disabled |
| | 0x0002 = enabled |

Third, the Read 3-Day Protocol is a command that returns: the Start Date value of the protocol as an RPC Date structure; the Pre-Meal Target Range value of the protocol as an RPC Target Range structure; the Post-Meal Target Range value of the protocol as an RPC Target Range structure; the Bedtime Target Range value of the protocol as an RPC Target Range structure. An exemplary command definition is as follows.

Command/Subcommand=0x8003

Input Parameters:
  None

Output Parameters:

| | |
|---|---|
| Start Date | RpcTime |
| Pre-meal Target Range | RpcTargetRange |
| Post-meal Target Range | RpcTargetRange |
| Bedtime Target Range | RpcTargetRange |

RPC Command Invocation:

| | |
|---|---|
| cmd-subcmd | RPC_CMD_READ_ST_CONFIGURATION \| RPC_SUBCMD_READ_3D_PROTOCOL |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_DATE |
| RpcDataArguments[0].length | Length of RpcDate structure in bytes |
| RpcDataArguments[0].value | RpcDate = start date value |
| RpcDataArguments[1].type | RPC_ARG_TYPE_TARGET_RANGE |
| RpcDataArguments[1].length | Length of RpcTargetRange structure in bytes |
| RpcDataArguments[1].value | RpcTargetRange = Pre-meal target range |
| RpcDataArguments[2].type | RPC_ARG_TYPE_TARGET_RANGE |
| RpcDataArguments[2].length | Length of RpcTargetRange structure in bytes |
| RpcDataArguments[2].value | RpcTargetRange = Post-meal target range |
| RpcDataArguments[3].type | RPC_ARG_TYPE_TARGET_RANGE |
| RpcDataArguments[3].length | Length of RpcTargetRange structure in bytes |
| RpcDataArguments[3].value | RpcTargetRange = Bedtime target range |

Fourth, the Read BIT Reminders is a command that shall return an array of ST Reminder structures. The number of ST Reminder structures returned is device dependent. The ID values for the returned structures shall be one of Administration or Acquisition. An exemplary command definition is as follows.

Command/Subcommand=0x8004
Input Parameters:
   None
Output Parameters:

| | |
|---|---|
| Reminder Array[ ] | RpcStReminder (section 6.1.2.8) |

RPC Command Invocation:

| | |
|---|---|
| cmd-subcmd | RPC_CMD_READ_ST_CONFIGURATION \| RPC_SUBCMD_READ_BIT_REMINDERS |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[n].value | RpcStReminder structure |

Fifth, the Read BIT Status is a command that returns an unsigned integer value which indicates whether the activation status is enabled or disabled; and the Exit Reason value as a 16 bit enumeration. An exemplary command definition is as follows.

Command/Subcommand=0x8005
Input Parameters:
   None
Output Parameters:

| | |
|---|---|
| Activation Status | OperationalState (See ISO/IEEE 11073-20601) |
| Exit Reason | UINT-16 |

RPC Command Invocation:

| | |
|---|---|
| cmd-subcmd | RPC_CMD_READ_ST_CONFIGURATION \| RPC_SUBCMD_READ_BIT_STATUS |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_OPERATIONAL_STATE |
| RpcDataArguments[0].length | 0.0002 |
| RpcDataArguments[0].value | 0x0001 = disabled |
| | 0x0002 = enabled |
| RpcDataArguments[1].type | RPC_ARG_TYPE_UINT16 |
| RpcDataArguments[1].length | 0.0002 |
| RpcDataArguments[1].value | Exit reason value |

Sixth, the Read BIT Protocol is a command that returns an array of RpcStParameter structures. Parameters contained in the array may include: the Start Date value of the protocol as an RPC Date structure; the Start Dosage value (IU) of the protocol as an 8 bit unsigned integer; the Maximum Dosage value (IU) of the protocol as an 8 bit unsigned integer; the Minimum Fasting Time value (number of hours) as an 8 bit unsigned integer; the Maximum Use Time value (number of days) as an 8 bit unsigned integer; the Completion Threshold value (mg/dL) of the protocol as a 16 bit unsigned integer; the Severe Hypo Threshold value (mg/dL) of the protocol as a 16 bit unsigned integer; the Hypo Threshold value (mg/dL) of the protocol as a 16 bit unsigned integer; the Maximum Severe Hypo Events value of the protocol as an 8 bit unsigned integer; the Maximum Hypo Events value of the protocol as an 8 bit unsigned integer; the Maximum Violation Events value of the protocol as an 8 bit unsigned integer; the Maximum Adherence Events value of the protocol as an 8 bit unsigned integer; the Doctor Phone Number value of the protocol as an Octet String of even length; the Daylight Saving Time status value of the protocol as a 16 bit enumeration value; the Minimum Period Length value (days) of the protocol as an 8 bit unsigned integer; and the Number of Primary Samples as an 8 bit unsigned integer. An exemplary command definition is as follows.

Command/Subcommand=0x8006
Input Parameters:
    None
Output Parameters:

| Parameter Array[ ] | RpcStParameter |
|---|---|

RPC Command Invocation:

| cmd-subcmd | RPC_CMD_READ_ST_CONFIGURATION \| RPC_SUBCMD_READ_BIT_PROTOCOL |
|---|---|
| RpcDataArguments[0].type | RPC_ARG_TYPE_EMPTY |
| RpcDataArguments[0].length | 0x0002 |
| RpcDataArguments[0].value | 0x0000 |

RPC Command Response:

| obj-handle | 0x0000 |
|---|---|
| event-time | 0xFFFFFFFF |
| event-type | MDC_NOTI_RPC_COMMAND_RESPONSE |
| RpcDataArguments[0].type | RPC_ARG_TYPE_ST_PARAMETER |
| RpcDataArguments[0].length | Length of RpcStParameter structure in bytes |
| RpcDataArguments[0].value | RpcStParameter = parameter ID and value |
| o | o |
| o | o |
| o | o |
| RpcDataArguments[n].type | RPC_ARG_TYPE_ST_PARAMETER |
| RpcDataArguments[0].length | Length of RpcStParameter structure in bytes |
| RpcDataArguments[0].value | RpcStParameter = parameter ID and value |

The parameters of a structure collection procedure can be changed by using the Set ST Configuration command in conjunction with the subcommands listed in this section. The command for setting ST configuration is RPC_CMD_SET_ST_CONFIGURATION and has a value of 0x8100. It must be "OR-ed" with one of the change setup subcommand values to form a complete command-subcommand value. Six exemplary subcommands are set forth below.

First, the Set 3-Day Reminders command shall set 3-Day time reminder values of the device to the values specified. The input parameter is an array of Structured Test time reminder structures. An agent device shall ignore any structures for which it has no corresponding ID. The ID values for the structures shall be one of Before Breakfast, Before Lunch, Before Dinner or Before Bedtime. The command returns an error code indicating success (RPC_ERR_NO_ERRORS) or failure. An exemplary command definition is as follows.

Command/Subcommand=0x8101
Input Parameters:

| Reminder Array [ ] | RpcStReminder (section 6.1.2.8) |
|---|---|

Output Parameters:

| Error Code | Number |
|---|---|

RPC Command Invocation:

| | |
|---|---|
| cmd-subcmd | RPC_CMD_SET_ST_CONFIGURATION \| RPC_SUBCMD_SET_3D_REMINDERS |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length fo RpcStReminder structure in bytes |
| RpcDataArguments[n].value | RpcStReminder structure |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Second, the Set 3-Day Status command shall set the 3-Day Activation status value of the device to the value specified. The input parameters is a 16 bit OperationalState value. The command returns an error code indicating success (RPC_ERR_NO_ERRORS) or failure. An exemplary command definition is as follows.

Command/Subcommand=0x8102

Input Parameters:

| | |
|---|---|
| Activation Status | OperationalState (See ISO/IEEE 11073-20601) |

Output Parameters:

| | |
|---|---|
| Error Code | Number |

RPC Command Invocation:

| | |
|---|---|
| cmd-subcmd | RPC_CMD_SET_ST_CONFIGURATION \| RPC_SUBCMD_SET_3D_STATUS |
| RpcDataArguments[0].type | RPC_ARG_TYPE_OPERATIONAL_STATE |
| RpcDataArguments[0].length | 0x0002 |
| RpcDataArguments[0].value | 0x0001 = disabled |
| | 0x0002 = enabled |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Third, the Set 3-Day Protocol command shall set the following protocol values of the device to the values specified:
1. The Start Date value of the protocol as an RPC Date structure.
2. The Pre-Meal Target Range value of the protocol as an RPC Target Range structure.
3. The Post-Meal Target Range value of the protocol as an RPC Target Range structure.
4. The Bedtime Target Range value of the protocol as an RPC Target Range structure.

An exemplary command definition is as follows.
Command/Subcommand=0x8103
Input Parameters:

| | |
|---|---|
| Start Date | Rpc Time |
| Pre-meal Target Range | Rpc Target Range |
| Post-meal Target Range | Rpc Target Range |
| Bedtime Target Range | Rpc Target Range |

Output Parameters:

| | |
|---|---|
| Error Code | Number |

RPC Command Invocation:

| | |
|---|---|
| cmd-subcmd | RPC_CMD_SET_ST_CONFIGURATION \| RPC_SUBCMD_SET_3D_PROTOCOL |
| RpcDataArguments[0].type | RPC_ARG_TYPE_DATE |
| RpcDataArguments[0].length | Length of RpcDate structure in bytes |
| RpcDataArguments[0].value | RpcDate=start date value |
| RpcDataArguments[1].type | RPC_ARG_TYPE_TARGET_RANGE |
| RpcDataArguments[1].length | Length of RpcTargetRange structure in bytes |
| RpcDataArguments[1].value | RpcTargetRange=Pre-meal target range |
| RpcDataArguments[2].type | RPC_ARG_TYPE_TARGET_RANGE |
| RpcDataArguments[2].length | Length of RpcTargetRange structure in bytes |
| RpcDataArguments[2].value | RpcTargetRange = Post-Meal target range |
| RpcDataArguments[3].type | RPC_ARG_TYPE_TARGET_RANGE |
| RpcDataArguments[3].length | Length of RpcTargetRange structure in bytes |
| RpcDataArguments[3].value | RpcTargetRange=Bedtime target range |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Fourth, the Set BIT Reminders command shall set BIT time reminder values of the device to the values specified. The input parameter is an array of Structured Test time reminder structures. An agent device shall ignore any structures for which it has no corresponding ID. The ID values for the structures shall be one of Administration or Acquisition. The command returns an error code indicating success (RPC_ERR_NO_ERRORS) or failure. An exemplary command definition is as follows.

Command/Subcommand=0x8104
Input Parameters:

| | |
|---|---|
| Reminder Array [ ] | RpcStReminder (section 6.1.2.8) |

Output Parameters:

| | |
|---|---|
| Error Code | Number |

RPC Command Invocation:

| | |
|---|---|
| cmd-subcmd | RPC_CMD_SET_ST_CONFIGURATION \| RPC_SUBCMD_SET_BIT_REMINDERS |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[0].value | RpcStReminder structure |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Fifth, the Set BIT Status command shall set the following BIT status values of the device: the Activation Status value as a 16 bit OperationalState; and the Exit Reason value as a 16 bit enumeration. The command returns an error code indicating success (RPC_ERR_NO_ERRORS) or failure. An exemplary command definition is as follows.

Command/Subcommand=0x8105

Input Parameters:

| Activation Status | OperationalState (See ISO/IEEE 11073-20601) |
|---|---|
| Exit Reason | UINT - 16 |

Output Parameters:

| Error Code | Number |
|---|---|

RPC Command Invocation:

| | |
|---|---|
| cmd-subcmd | RPC_CMD_SET_ST_CONFIGURATION \| RPC_SUBCMD_SET_BIT_STATUS |
| RpcDataArguments[0].type | RPC_ARG_TYPE_OPERATIONAL_STATE |
| RpcDataArguments[0].length | 0x0002 |
| RpcDataArguments[0].value | 0x0001 = disabled |
| | 0x0002 = enabled |
| RpcDataArguments[1].type | RPC_ARG_TYPE_UINT16 |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Sixth, the Set BIT Protocol command shall set BIT protocol values of the device to the values specified. The input parameter is an array of Structured Test parameter structures. An agent device shall ignore any structures for which it has no corresponding parameter ID. The command returns an error code indicating success (PRC_ERR_NO_ERRORS) or failure. An exemplary command definition is as follows.

Command/Subcommand=0x8106

Input Parameters:

| Reminder Array [ ] | RpcStParameter (section 6.1.2.9) |
|---|---|

Output Parameters:

| Error Code | Number |
|---|---|

RPC Command Invocation:

| | |
|---|---|
| cmd-subcmd | RPC_CMD_READ_ST_CONFIGURATION \| RPC_SUBCMD_SET_BIT_PROTOCOL |
| RpcDataArguments[0].type | RPC_ARG_TYPE_ST_PARAMETER |
| RpcDataArguments[0].length | Length of RpcStParameter structure in bytes |
| RpcDataArguments[0].value | RpcStParameter structure |
| o | o |
| o | o |
| o | o |
| RpcDataArguments[n].type | RPC_ARG_TYPE_ST_PARAMETER |
| RpcDataArguments[n].length | Length of RpcStParameter structure in bytes |
| RpcDataArguments[n].value | RpcStParameter structure |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0.0002 |
| RpcDataArguments[0].value | Error code enumeration value |

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

APPENDIX A

Common RPC Numeric Object Attributes

| Attribute Name | Value | Qualifier |
|---|---|---|
| Handle | The Handle attribute represents a reference ID for this object. Each object shall have a unique ID assigned by the agent. | M |
| Type | Defined in each of the numeric objects. | M |
| Metric-Spec-Small | mss-avail-intermittent \| mss-avail-stored-data \| mss-upd-aperiodic \| mss-msmt-aperiodic \| mssacc-agent-initiated \| mss-cat-manual. | M |
| Unit-Code | Defined in each of the numeric objects. | O |
| Attribute-Value-Map | Defined in each of the numeric objects | M |
| Absolute-Time-Stamp | AbsoluteTime as defined in ISO/IEEE 11073-20601 | M |
| Basic-Nu-Observed-Value | This attribute defines the numerical observed value of the object, without any further embedded status information, but with a smaller numerical representation compared to Simple-Nu-Observed-Value. One and only one of Simple-Nu-Observed-Value, Basic-Nu-Observed-Value or Nu-Observed-Value shall be present. | C |
| Simple-Nu-Observed-Value | This attribute defines the numerical observed value of the object, without any further embedded status information as found in Nu-Observed-Value. One and only one of Simple-Nu-Observed-Value, Basic-Nu-Observed-Value, or Nu-Observed-Value shall be present. | C |
| Nu-Observed-Value | This attribute defines the numerical observed value of the object and combines it with measurement status and unit information. It is used when status/unit are dynamic and are always provided together with the value. One and only one of Simple-Nu-Observed-Value, Basic-Nu-Observed-Value or Nu-Observed-Value shall be present | |

Pen/Syringe Insulin ID

| Attribute Name | Value | Qualifier |
| --- | --- | --- |
| Type | MDC_PART_OBJ MDC_CTXT_RPC_PENSYR_INS_ID | M |
| Attribute-Value-Map | MDC_ATTR_NU_BAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601 - This indicates the Insulin ID value, ranging from 1 to 255 | M |

Pen/Syringe Insulin Bolus Amount

| Attribute Name | Value | Qualifier |
| --- | --- | --- |
| Type | MDC_PART_OBJ MDC_CTXT_RPC_PENSYR_BOLUS_AMT | M |
| Unit-Code | MDC_DIM_X_INTL_UNIT | M |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601 - This indicates a pen/syringe insulin dose in International Units (IU), ranging from 0.0 to 999.9 | M |

Insulin Bolus Recommendation

| Attribute Name | Value | Qualifier |
| --- | --- | --- |
| Type | MDC_PART_OBJ \| MDC_CTXT_RPC_BOLUS_RECOMMENDATION | M |
| Unit-Code | MDC_DIM_X_INTL_UNIT | M |
| Attribute-Value-Map | MDC_ATTR_NU_ AL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601 - This indicates a pen/syringe insulin dose in International Units (IU), ranging from 0.0 to 999.9 | M |

Pump Insulin Bolus Amount

| Attribute Name | Value | Qualifier |
| --- | --- | --- |
| Type | MDC_PART_OBJ \| MDC_CTXT_RPC_PUMP_BOLUS_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601 - This indicates a pump insulin dose in International Units (IU), ranging from 0.0 to 999.9 | M |

Pump Temporary Basal Rate

| Attribute Name | Value | Qualifier |
| --- | --- | --- |
| Type | MDC_PART_OBJ \| MDC_CTXT_RPC_PUMP_TEMP_BASAL_RATE | M |
| Unit-Code | MDC_DIM_X_INTL_UNIT_PER_HR \| MDC_DIM_PERCENT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |

-continued

| Attribute Name | Value | Qualifier |
|---|---|---|
| Basic-Nu-Observed-Value | See ISO/IEEE 11073-20601 - This indicates the insulin pump's temporary basal rate in International Units per hour (IU/hr), ranging from 0.0 to 999.9, or as a percentage ranging from 0.0 to 100.0 | M |

Pump Temporary Basal Duration
Insulin pump's temporary basal duration BCD Number (hhmm) 0x0000-0x9959

| Attribute Name | Value | Qualifier |
|---|---|---|
| Type | MDC_PART_OBJ \| MDC_CTXT_RPC_PUMP_TEMP_BASAL_DURATION | M |
| Unit-Code | | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601 - This indicates the insulin pump's temporary basal duration in hours and minutes (BDC format). | M |

Pump Wave Amount

| Attribute Name | Value | Qualifier |
|---|---|---|
| Type | MDC_PART_OBJ \| MDC_CTXT_RPC_PUMP_WAVE_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601 - This indicates the insulin pump's wave amount in International Units (IU), ranging from 0.0 to 999.9 | M |

Pump Wave Duration
Insulin Pump's Wave Duration BCD Number (hhmm) 0x0000-0x9959

| Attribute Name | Value | Qualifier |
|---|---|---|
| Type | MDC_PART_OBJ \| MDC_CTXT_RPC_PUMP_WAVE_DURATION | M |
| Unit-Code | | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601 - This indicates the insulin pump's wave duration in hours and minutes (BCD format). | M |

APPENDIX B

Common RPC Enumeration Object Attributes

| Attribute Name | Value | Qualifier |
|---|---|---|
| Handle | The Handle attribute represents a reference ID for this object. Each object shall have a unique ID assignment by the agent. | M |
| Type | Defined in each of the enumeration objects. | M |

-continued

| Attribute Name | Value | Qualifier |
|---|---|---|
| Metric-Spec-Small | mss-avail-intermittent \| mss-avail-stored-data \| mss-upd-aperiodic \| mssacc-agent-initiated \| mss-cat-manual. | M |
| Attribute-Value-Map | Defined in each of the enumeration objects. | M |
| Absolute-Time-Stamp | AbsoluteTime as defined in ISO/IEEE 11072-20601 | M |
| Enum-Observed-Value-Simple-OID | The value is reported as a nomenclature code. One and only one of Enum-Observed-Value-Simple-OID, Enum-Observed-Value-Basic-Bit-Str shall be present | C |
| Enum-Observed-Value-Basic-Bit-Str | The value is reported as a bit string of 32-bits. One and only one of Enum-Observed-Value-Simple-OID, Enum-Observed-Value-Basic-Bit-Str, Enum-Observed-Value-Simple-Str shall be present. | C |
| Enum-Observed-Value-Simple-Str | The value is reported as an ASCII printable string. One and only one of Enum-Observed-Value-Simple-OID, Enum-Observed-Value-Basic-Bit-Str, Enum-Observed-Value-Simple-Str shall be present | C |

Timeblock (Meal Segment)

| Attribute Name | Value | Qualifier |
|---|---|---|
| Type | MDC_PART_OBJ \| MDC_CTXT_RPC_MEAL_SEG_TIMEBLOCK | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_MEAL_SEG_TIME_NT RPC_MEAL_SEG_TIME_BB RPC_MEAL_SEG_TIME_AB RPC_MEAL_SEG_TIME_BL RPC_MEAL_SEG_TIME_AL RPC_MEAL_SEG_TIME_BD RPC_MEAL_SEG_TIME_AD RPC_MEAL_SEG_TIME_EV | M |

Structured Test Type

| Attribute Name | Value | Qualifier |
|---|---|---|
| Type | MDC_PART_OBJ \| MDC_CTXT_RPC_ST_TYPE | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_STRUCTURED_TEST_3_DAY_SNAP \| RPC_STRUCTURED_TEST_BIT | M |

Structured Test Time Event

| Attribute Name | Value | Qualifier |
|---|---|---|
| Type | MDC_PART_OBJ \| MDC_CTXT_RPC_MEAL_SEG_TIME_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_TIME_EVENT_BB RPC_ST_TIME_EVENT_AB RPC_ST_TIME_EVENT_BL RPC_ST_TIME_EVENT_AL RPC_ST_TIME_EVENT_BD RPC_ST_TIME_EVENT_AD RPC_ST_TIME_EVENT_BT | M |

Structured Test Protocol Events

| Attribute Name | Value | Qualifier |
|---|---|---|
| Type | MDC_PART_OBJ \| MDC_CTXT_RPC_ST_PROTOCOL_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_MISSED_BG_ACQUISITION RPC_ST_MISSED_INSULIN_ADMINISTRATION RPC_ST_EXIT_NO_REASON RPC_ST_EXIT_TIME_LIMIT_EXCEEDED RPC_ST_EXIT_GOAL_REACHED RPC_ST_EXIT_TOO_MANY_SEVEREHYPOS RPC_ST_EXIT_TOO_MANY_HYPOS RPC_ST_EXIT_ADHERENCE RPC_ST_EXIT_PROTOCOL RPC_ST_EXIT_MAXIMUMDOSE RPC_ST_EXIT_INVALIDDATETIME RPC_ST_EXIT_INVALIDPARAM | M |

Structured Test Configuration Change

| Attribute Name | Value | Qualifier |
|---|---|---|
| Type | MDC_PART_OBJ \| MDC_CTXT_RPC_ST_CONFIG_CHANGE | M |
| Unit-Code | | O |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | See section 6.1.1.19 for Structured Test Parameter definitions | M |

What is claimed is:

1. A computer-implemented diabetes management system for configuring a structured collection procedure implemented on a collection device, comprising:
a meter housed by the collection device that measures the concentration of glucose in blood;
a collection application implemented as computer executable instructions in a data store of the collection device, the collection application executes a structured collection procedure for obtaining measurement data from the meter and provides access to the measurement data in accordance with a communication protocol, wherein the structured collection procedure specifies a schedule of collection events for obtaining measures of glucose using the meter and defines parameters including an operational status for the structured collection procedure, reminders for the specified collection events, a start date for the structure collection procedure, a pre-meal target range for measurement data from the meter, a post-meal target range for measurement data from the meter and a bedtime target ranges for measurement data from the meter;
a configuration application that accesses and manipulates the parameters of the structured collection procedure using a set of action commands which are defined as a private extension of IEEE standard 11073-20601, wherein the set of action commands includes a first command to read the operational status, a second command to set the operational status, a third command to read the reminders for the specified collection events, a fourth command to set a reminder for a given collection event associated with the structured collection procedure, a fifth command to read the start date, the pre-meal target range, the post-meal target range and the bedtime target range, and a sixth command to set one of the start date, the pre-meal target range, the post-meal target range and the bedtime target range; and
a collection interface implemented as computer executable instructions in a data store of the collection device that receives an action command from the configuration application, executes the received action command and issues a response command in response thereto, wherein the response command is defined in compliance with the communication protocol.

2. The system of claim 1 wherein the set of action commands are defined as a private extension of the communication protocol.

3. The system of claim 1 wherein the collection application includes an instance of an object pertaining to the meter.

4. The system of claim 1 wherein the configuration application resides on a computing device distinct from the collection device and communicates via a wireless communication link with the collection device.

5. A computer-implemented system for configuring a structured collection procedure implemented on a collection device, comprising:
a meter that measures a physiological variable of a person;
a collection application implemented as computer executable instructions in a data store of the collection device, the collection application operable to execute a structured collection procedure to obtain a physiological variable from a patient and to provide access to the physiological variable in accordance with a communication protocol, wherein the structured collection procedure specifies a schedule of collection events for obtaining measures of glucose using the meter and defines parameters including an operational status for the structured collection procedure and reminders for the specified collection events;

a configuration application implemented as computer executable instructions that access and manipulate the parameters of the structured collection procedure using a set of action commands which are defined as a private extension of IEEE standard 11073-20601, wherein the set of action commands includes a first command to read the operational status, a second command to set the operational status, a third command to read the reminders for the specified collection events, a fourth command to set a reminder for a given collection event associated with the structured collection procedure; and a collection interface implemented as computer executable instructions in a data store of the collection device that receives an action command from the configuration application, executes the received action command and issues a response command in response thereto.

6. The system of claim 5 wherein an additional parameter of the structured collection procedure is selected from the group consisting of: a start date for the collection procedure, a pre-meal target range for measurement data from the meter, a post-meal target range for measurement data from the meter and a bedtime target ranges for measurement data from the meter.

7. The system of claim 5 wherein the set of action commands are defined as a private extension of the communication protocol.

8. The system of claim 5 wherein the collection application includes an instance of an object pertaining to the meter.

9. The system of claim 5 wherein the configuration application resides on a computing device distinct from the collection device and communicates via a wireless communication link with the collection device.

* * * * *